United States Patent
Sullivan et al.

(10) Patent No.: US 9,757,581 B2
(45) Date of Patent: Sep. 12, 2017

(54) WEARABLE CARDIOVERTER DEFIBRILLATOR COMPONENTS MAKING AGGREGATE SHOCK/NO SHOCK DETERMINATION FROM TWO OR MORE ECG SIGNALS

(71) Applicant: West Affum Holdings Corp., Grand Cayman (KY)

(72) Inventors: Joseph L. Sullivan, Kirkland, WA (US); Robert P. Marx, Jr., Kent, WA (US); David P. Finch, Bothell, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 0 days.

(21) Appl. No.: 15/142,656

(22) Filed: Apr. 29, 2016

(65) Prior Publication Data

US 2016/0243374 A1 Aug. 25, 2016

Related U.S. Application Data (62) Division of application No. 15/051,430, filed on Feb. 23, 2016, which is a division of application No. 14/461,670, filed on Aug. 18, 2014.

(Continued)

(51) Int. Cl.
*A61N 1/39* (2006.01)
*A61N 1/02* (2006.01)
(Continued)

(52) U.S. Cl.
CPC .......... *A61N 1/3987* (2013.01); *A61B 5/0464* (2013.01); *A61B 5/6805* (2013.01);
(Continued)

(58) Field of Classification Search
CPC ................................................... A61B 5/6843
(Continued)

(56) References Cited

U.S. PATENT DOCUMENTS

| 3,724,455 A | 4/1973 | Unger |
| 4,583,524 A | 4/1986 | Hutchins |

(Continued)

FOREIGN PATENT DOCUMENTS

| WO | 9839061 A2 | 9/1998 |
| WO | 2012064604 A1 | 5/2012 |

OTHER PUBLICATIONS

ZOLL LifeVest Model 4000 Patient Manual PN 20B0047 Rev B, (C) 2009-2012.

(Continued)

*Primary Examiner* — Carl H Layno
*Assistant Examiner* — Erin M Piateski
(74) *Attorney, Agent, or Firm* — Kavounas Patent Law Office, PLLC (57) ABSTRACT

Components of wearable cardiac defibrillator (WCD) systems, software, and methods are provided. A WCD system includes a support structure that a patient can wear and electrodes that can capture at least two of the patient's ECG signals. A component includes an energy storage module that can store an electrical charge, a discharge circuit, and a processor that can make a shock/no shock determination, and cause the discharge circuit to discharge the stored charge, if the determination is to shock. In some embodiments, the processor discards at least one of the ECG signals prior to making the shock/no shock determination. The determination can be made from the remaining one or more ECG signals. In some embodiments, the processor makes an aggregate shock/no shock determination from two or more of the ECG signals.

12 Claims, 8 Drawing Sheets

MAKING SHOCK/NO SHOCK
DETERMINATIONS FROM
MULTI-VECTOR ECG SIGNALS

Related U.S. Application Data (60) Provisional application No. 61/002,841, filed on May 13, 2014.

(51) Int. Cl.
  *A61N 1/04* (2006.01)
  *A61B 5/00* (2006.01)
  *A61B 5/0464* (2006.01)

(52) U.S. Cl.
  CPC ............ *A61B 5/7221* (2013.01); *A61N 1/025* (2013.01); *A61N 1/046* (2013.01); *A61N 1/0484* (2013.01); *A61N 1/39* (2013.01); *A61N 1/3918* (2013.01); *A61N 1/3925* (2013.01)

(58) Field of Classification Search
  USPC ............................................................ 607/5
  See application file for complete search history.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1* | 9/2001 | Snyder ................. A61B 5/0428 600/509 |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,529,875 B1 | 3/2003 | Nakajima | |
| 6,546,285 B1 | 4/2003 | Owen et al. | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,140,154 B2 | 3/2012 | Donnelly et al. | |
| 8,369,944 B2 | 2/2013 | Macho et al. | |
| 8,644,925 B2 | 2/2014 | Volpe et al. | |
| 8,676,313 B2 | 3/2014 | Volpe et al. | |
| 8,965,500 B2 | 2/2015 | Macho et al. | |
| 9,008,801 B2 | 4/2015 | Kaib et al. | |
| 9,131,901 B2 | 9/2015 | Volpe et al. | |
| 9,132,267 B2 | 9/2015 | Kaib | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Volpe et al. | |
| 2009/0005827 A1 | 1/2009 | Weintraub et al. | |
| 2010/0007413 A1* | 1/2010 | Herleikson .......... A61B 5/0424 330/124 R |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1* | 11/2011 | Kaib .................... A61B 5/0006 607/5 |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0302860 A1 | 11/2012 | Volpe et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2016/0004831 A1 | 1/2016 | Carlson et al. | |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

Heartstart MRx and XL AED Algorithm—Application Note, Jul. 2001, Edition 2 Philips Healthcare, USA.

* cited by examiner

WEARABLE CARDIAC DEFIBRILLATOR (WCD) SYSTEM WITH COMPONENT

ELECTRODES & ECG SIGNALS
ALONG MULTIPLE VECTORS

*DISCARDING ECG SIGNAL(S) BEFORE SHOCK/NO SHOCK DETERMINATION*

FIG. 9 *METHODS*

FIG. 10 *MULTI-VECTOR COMBINATION*

WEARABLE CARDIOVERTER DEFIBRILLATOR COMPONENTS MAKING AGGREGATE SHOCK/NO SHOCK DETERMINATION FROM TWO OR MORE ECG SIGNALS

CROSS REFERENCE TO RELATED PATENT APPLICATIONS

This patent application is a divisional of U.S. patent application Ser. No. 15/051,430, filed on Feb. 23, 2016, which in turn is a divisional of U.S. patent application Ser. No. 14/461,670, filed on Aug. 18, 2014, abandoned on Jun. 30, 2016, which in turn claims priority from U.S. Provisional Patent Application Ser. No. 61/992,841, filed on May 13, 2014, the disclosure of which is hereby incorporated by reference for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. These people receive the recommendation to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardiac defibrillator ("WCD") system. A wearable defibrillator system typically includes a harness, vest, or other garment for wearing by the patient. The system includes a defibrillator and external electrodes, which are attached on the inside of the harness, vest, or other garment. When the person wears the system, the external electrodes may then make good electrical contact with the person's skin, and therefore can help monitor the person's ECG. If a shockable heart arrhythmia is detected, then the defibrillator delivers the appropriate electric shock through the person's body, and thus through the heart.

BRIEF SUMMARY

The present description gives instances of components of wearable cardiac defibrillator systems, software, and methods, the use of which may help overcome problems and limitations of the prior art.

In embodiments, a component of a wearable cardiac defibrillation system is provided. The system includes a support structure that a patient can wear and electrodes that can capture at least two of the patient's ECG signals. The component includes an energy storage module that can store an electrical charge, a discharge circuit, and a processor that can make a shock/no shock determination, and cause the discharge circuit to discharge the stored charge, if the determination is to shock.

In some embodiments, the processor discards at least one of the ECG signals prior to making the shock/no shock determination. The determination can be made from the remaining one or more ECG signals.

In some embodiments, the processor makes an aggregate shock/no shock determination from two or more ECG signals.

An advantage over the prior art is that the shock/no shock determination can be made with better information, and therefore have a better chance of being correct for the occasion. These and other features and advantages of this description will become more readily apparent from the Detailed Description, which proceeds with reference to the associated drawings in which:

DETAILED DESCRIPTION

As has been mentioned, the present description is about components of wearable cardiac defibrillator systems, software, and methods. Embodiments are now described in more detail.

A wearable cardiac defibrillator (WCD) system made according to embodiments has a number of components. These components can be provided separately as modules that can be interconnected, or can be combined with other components, etc.

A component of a WCD system can be a support structure, which is configured to be worn by the patient. The support structure can be any structure suitable for wearing, such as a harness, a vest, one or more belts, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around at least the torso. Other embodiments could use an adhesive structure or another way for attaching to the person, without encircling any part of the body. There can be other examples.

Figure 1:
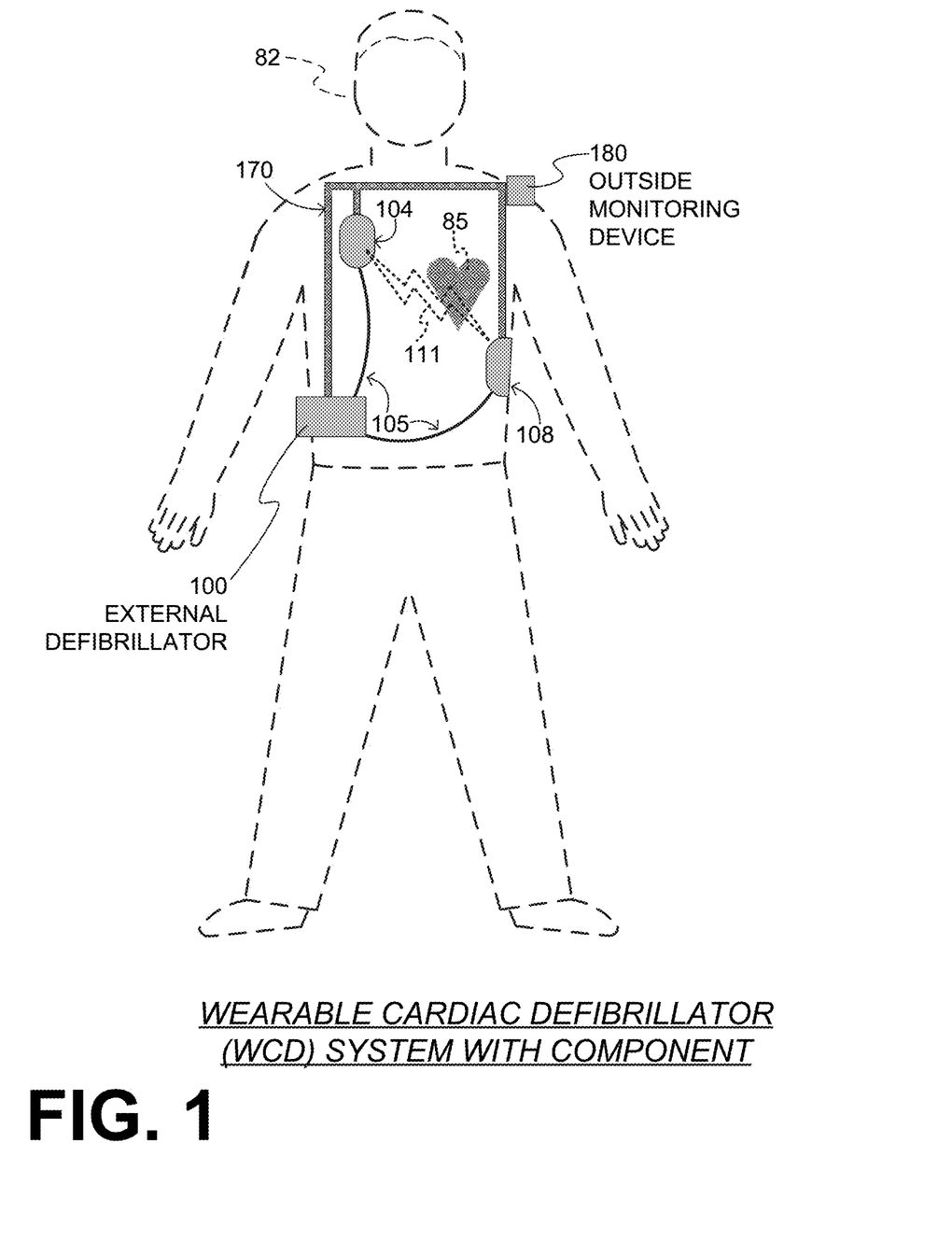
FIG. 1 is a diagram of components of a sample wearable defibrillator system, made according to embodiments.

FIG. 1 depicts components of a wearable defibrillator system made according to embodiments, as it might be worn by a person 82. A person such as person 82 may also be referred to as a patient and/or wearer, since that person wears components of the wearable defibrillator system.

In FIG. 1, a generic support structure 170 is shown relative to the body of person 82, and thus also relative to his or her heart 85. Structure 170 could be a harness, a vest, one or more belts, or a garment, etc., as per the above. Structure 170 could be implemented in a single component, or multiple components, and so on. Structure 170 is wearable by person 82, but the manner of wearing it is not depicted, as structure 170 is depicted only generically in FIG. 1.

A wearable defibrillator system is configured to defibrillate the patient, by delivering electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of person 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of person 82. Pulse 111 can also be one or more pacing pulses, and so on.

A prior art defibrillator typically decides whether to defibrillate or not based on an electrocardiogram ("ECG") signal of the patient. However, defibrillator 100 can defibrillate, or not defibrillate, also based on other inputs.

The wearable defibrillator system may optionally include an outside monitoring device 180. Device 180 is called an "outside" device because it is provided as a standalone device, for example not within the housing of defibrillator 100. Device 180 can be configured to monitor at least one local parameter. A local parameter can be a parameter of patient 82, or a parameter of the wearable defibrillation system, or a parameter of the environment, as will be described later in this document.

Optionally, device 180 is physically coupled to support structure 170. In addition, device 180 can be communicatively coupled with other components, which are coupled to support structure 170. Such a component can be a communication module, as will be deemed applicable by a person skilled in the art in view of this disclosure.

Figure 2:
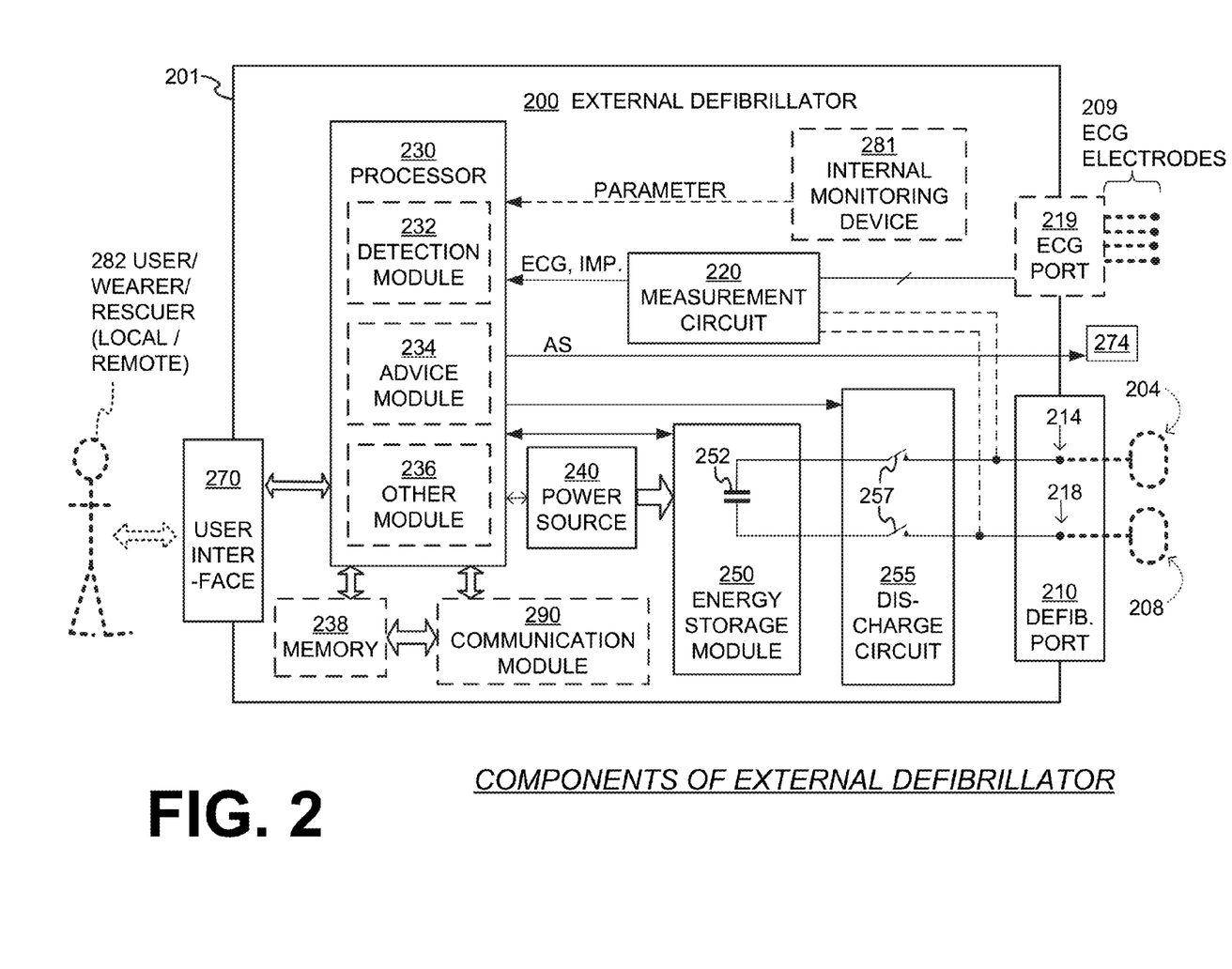
FIG. 2 is a diagram showing sample components of an external defibrillator, such as the one in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which is also known as casing 201.

External defibrillator 200 is intended for a patient who would be wearing it, such as person 82 of FIG. 1. Defibrillator 200 may further include a user interface 270 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the wearable defibrillator system.

User interface 270 can be made in any number of ways. User interface 270 may include output devices, which can be visual, audible or tactile, for communicating to a user. User interface 270 may also include input devices for receiving inputs from users. For example, interface 270 may include a screen, to display what is detected and measured, provide visual feedback to rescuer 282 for their resuscitation attempts, and so on. Interface 270 may also include a speaker, to issue voice prompts, etc. Sounds, images, vibrations, and anything that can be perceived by user 282 can also be called human perceptible indications. Interface 270 may additionally include various controls, such as pushbuttons, keyboards, touchscreens, a microphone, and so on. In addition, discharge circuit 255 can be controlled by processor 230, or directly by user 282 via user interface 270, and so on.

Defibrillator 200 may include an internal monitoring device 281. Device 281 is called an "internal" device because it is incorporated within housing 201. Monitoring device 281 can monitor patient parameters, patient physiological parameters, system parameters and/or environmental parameters, all of which can be called patient data. In other words, internal monitoring device 281 can be complementary or an alternative to outside monitoring device 180 of FIG. 1. Allocating which of the system parameters are to be monitored by which monitoring device can be done according to design considerations.

Patient physiological parameters include, for example, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device could include a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. Pulse detection is taught at least in Physio-Control's U.S. Pat. No. 8,135,462, which is hereby incorporated by reference in its entirety. In addition, a person skilled in the art may implement other ways of performing pulse detection.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 82 will know about a condition that is either not improving or deteriorating.

Patient state parameters include recorded aspects of patient 82, such as motion, posture, whether they have spoken recently plus maybe also what they said, and so on, plus optionally the history of these parameters. Monitoring device 180 or monitoring device 281 may include a motion detector, which can be made in many ways as is known in the art. For example, accelerometers make good motion detectors. Or, one of these monitoring devices could include a location sensor such as a Global Positioning System (GPS), which informs of the location, and the rate of change of location over time. Many motion detectors output a motion signal that is indicative of the motion of the detector, and thus of the patient's body. Patient state parameters can be very helpful in narrowing down the determination of whether SCA is indeed taking place.

System parameters of a wearable defibrillation system can include system identification, battery status, system date and time, reports of self-testing, records of data entered, records of episodes and intervention, and so on.

Environmental parameters can include ambient temperature and pressure. A humidity sensor may provide information as to whether it is likely raining. Presumed patient location could also be considered an environmental parameter. The patient location could be presumed if monitoring device 180 or 281 includes a GPS sensor.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged in defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250. The electric charge will be the shock for defibrillation, pacing, and so on.

Defibrillator 200 may optionally also have an ECG port 219 in housing 201, for plugging in sensing electrodes 209, which are also known as ECG leads. It is also possible that Sensing electrodes 209 can be connected continuously to ECG port 219, instead. Sensing electrodes 209 can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a wearable defibrillator system according to embodiments also includes a fluid that it can deploy automatically between the electrodes and the patient skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a wearable defibrillator system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated responsive to receiving activation signal AS from processor 230, prior to the electrical discharge.

It will be appreciated, then, that the electrodes of a WCD system include both the defibrillation electrodes that can transport the electrical charge for defibrillation purposes, and also the sensing electrodes that are configured to capture the ECG signals of the patient. Moreover, with proper design, a single electrode can perform both functions.

Figure 3:
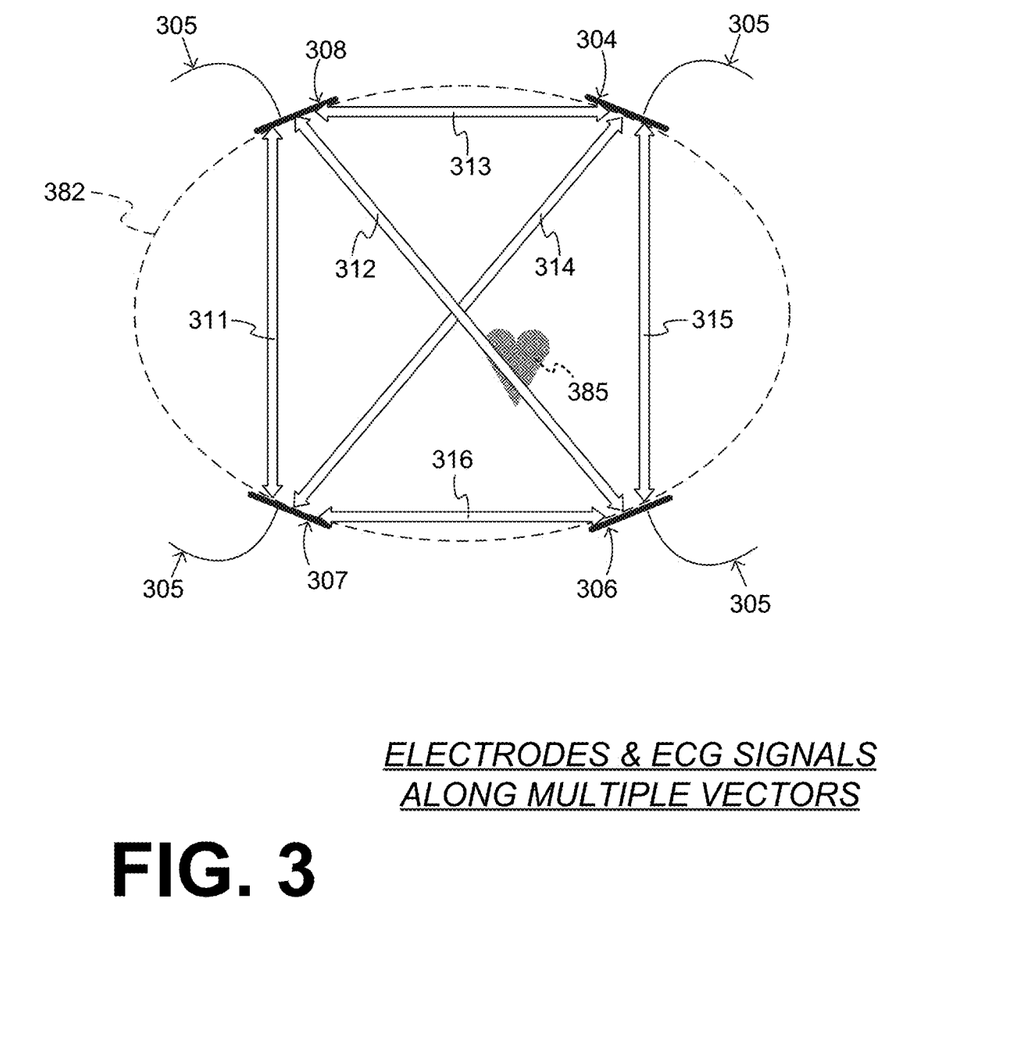
FIG. 3 is a conceptual diagram for illustrating an example how different electrodes may capture ECG signals along different vectors according to embodiments.

FIG. 3 is a conceptual diagram for illustrating how electrodes of a WCD system may capture ECG signals along different vectors according to embodiments. A section of a patient 382 having a heart 385 is shown. There are four electrodes 304, 306, 307, 308, attached to the torso, each with a wire lead 305. Any pair of these electrodes defines a vector across with an ECG signal may be measured. The four electrodes 304, 306, 307, 308 therefore can define six vectors, across which six respective ECG signals 311, 312, 313, 314, 315, 316 can be captured. FIG. 3 thus illustrates a multi-vector situation. In FIG. 3 it will be understood that electrodes 304, 306, 307, 308 are drawn on the same plane for simplicity, while that is not necessarily the case. Accordingly, the vectors of ECG signals 311, 312, 313, 314, 315, 316 are not necessarily on the same plane, either.

Any one of ECG signals 311, 312, 313, 314, 315, 316 might provide sufficient data for making a good shock/no shock determination. The effort is to shock when needed, and not shock when not needed. The problem is that, at any given point in time, some of these ECG signals may include noise, while others not. The noise may be due to patient movement or how the electrode contacts the skin. The noise problem for a WCD may be further exacerbated by the desire to use dry, non-adhesive monitoring electrodes. Dry, non-adhesive electrodes are thought to be more comfortable for the patient to wear, but may produce more noise than a conventional ECG monitoring electrode that includes adhesive to hold the electrode in place and an electrolyte gel to reduce the impedance of the electrode-skin interface. In order make the best shock/no-shock determination as correctly as possible, a WCD may assess which of ECG signals 311, 312, 313, 314, 315, 316 is best for rhythm analysis and ECG interpretation.

Returning to FIG. 2, defibrillator 200 also includes a measurement circuit 220. Measurement circuit 220 receives physiological signals from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the patient's ECG signal can be sensed as a voltage difference between electrodes 204, 208. Plus, impedance between electrodes 204, 208 and/or the connections of ECG port 219 can be sensed. Sensing the impedance can be useful for detecting, among other things, whether these electrodes 204, 208 and/or sensing electrodes 209 are not making good electrical contact with the patient's body. These physiological signals can be sensed, and information about them can be rendered by circuit 220 as data, other signals, etc.

Defibrillator 200 also includes a processor 230. Processor 230 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 can be considered to have a number of modules. One such module can be a detection module 232. Detection module 232 can include a ventricular fibrillation ("VF") detector. The patient's sensed ECG from measurement circuit 220 can be used by the VF detector to determine whether the patient is experiencing VF. Detecting VF is useful, because VF results in SCA.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm.

The shock/no shock determination can be made from one or more of the captured ECG signals according to embodiments. An example is now described.

Figure 4:
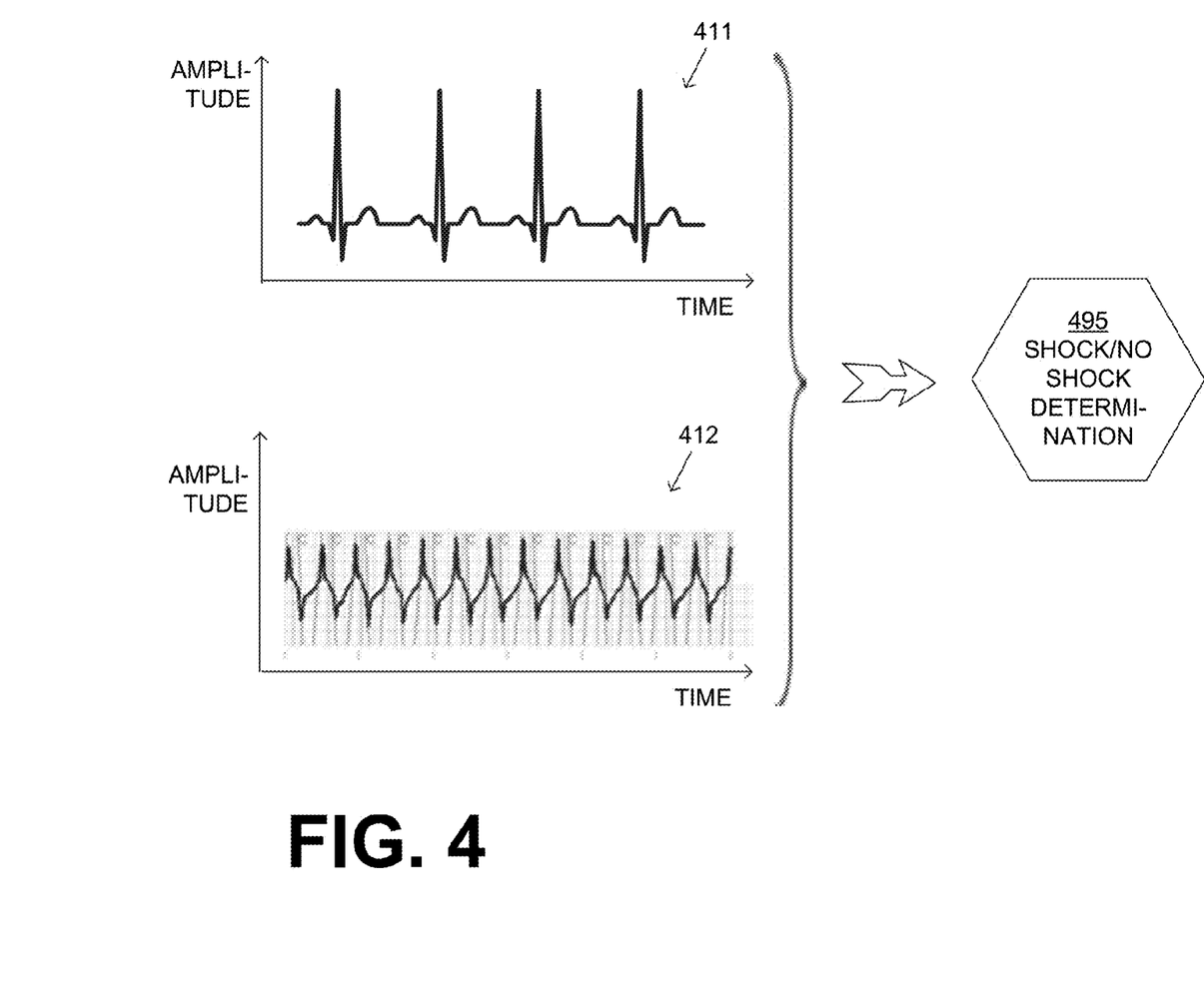
FIG. 4 is a conceptual diagram for illustrating that different possible ECG signals can be used to arrive at a shock/no shock determination according to embodiments.

FIG. 4 shows the time waveforms 411, 412 of two sample ECG signals. Waveform 411 is from an ECG signal of a heart in a normal sinus rhythm. Waveform 412 is from an ECG signal of a heart undergoing asystole with compression artifact. According to embodiments, processor 230 can make a shock/no shock determination 495 from such ECG signals, and any other available ones, as is described later in this document. In FIG. 4, waveforms 411, 412 are chosen because they make good samples individually; however, the exact situation of FIG. 4 does not necessarily occur often, as either one of waveforms 411, 412 could be further distorted by noise, etc.

Returning to FIG. 2, if the determination is to shock, processor 230 can cause discharge circuit 255 to discharge the electrical charge stored in energy storage module 250 through at least two of the electrodes 204, 208 so as to defibrillate the patient. Discharging is also called delivering the electrical charge. Discharging can be also for pacing instead of for defibrillation, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, volatile memories, nonvolatile memories (NVM), read-only memories (ROM), random access memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read, and execute. More particularly, the programs can include sets of instructions in the form of code, which processor 230 may be able to execute upon reading. Executing is performed by physical manipulations of physical quantities, and may result in the functions, processes, actions and/or methods to be performed, and/or the processor to cause other devices or components or blocks to perform such functions, processes, actions and/or methods. The programs can be operational for the inherent needs of processor 230, and can also include protocols and ways that decisions can be made by advice module 234. In addition, memory 238 can store prompts for user 282, if they are a local rescuer. Moreover, memory 238 can store data. The data can include patient data, system data and environmental data, for example as learned by internal monitoring device 281 and outside monitoring device 180.

The data can be stored in memory 238 before it is transmitted out of defibrillator 200, or stored there after it is received by it.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230.

Defibrillator 200 additionally includes an energy storage module 250, which can thus be coupled to the support structure of the wearable system. Module 250 is where some electrical energy is stored in the form of an electrical charge, when preparing it for sudden discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the energy in the form of electrical charge, for delivering to the patient.

Defibrillator 200 moreover includes a discharge circuit 255. Circuit 255 can be controlled via processor 230 or user interface 270. When so controlled, circuit 255 can permit the energy stored in module 250 to be discharged to nodes 214, 218, and thus also to defibrillation electrodes 204, 208. Circuit 255 can include one or more switches 257. Switches 257 can be made in a number of ways, such as by an H-bridge, and so on.

Defibrillator 200 can optionally include a communication module 290, for establishing one or more wired or wireless communication links with other devices of other entities, such as a remote assistance center, Emergency Medical Services (EMS), and so on. Module 290 may also include an antenna, portions of a processor, and other sub-components as may be deemed necessary by a person skilled in the art. This way, data and commands can be communicated, such as patient data, event information, therapy attempted, CPR performance, system data, environmental data, and so on.

Defibrillator 200 can optionally include other components.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary, however, and there may be cases where modules are equivalently aggregated into a single program, even with unclear boundaries. In some instances, software is combined with hardware, in a mix called firmware.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 5:
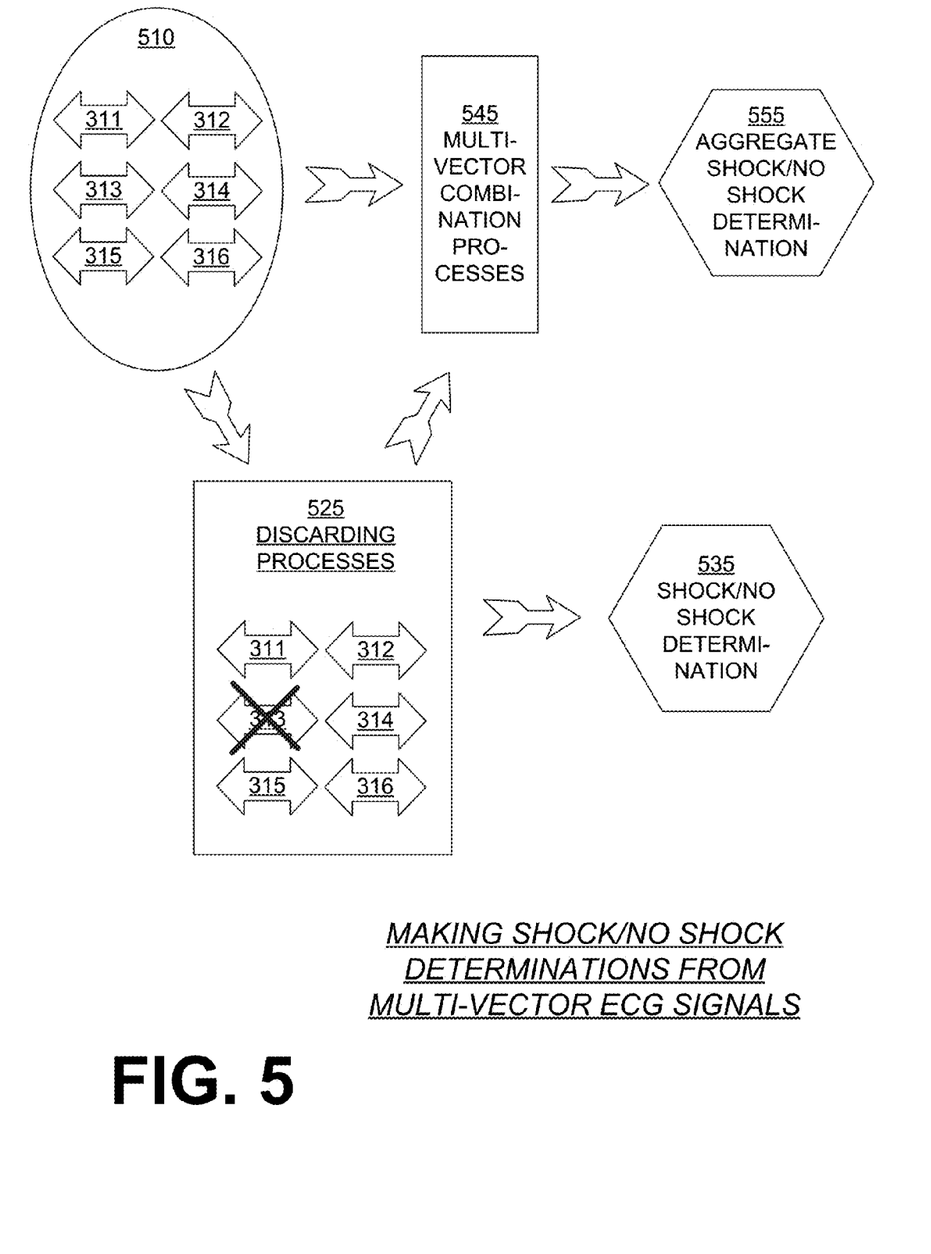
FIG. 5 is a conceptual diagram for illustrating different types of processes according to embodiments.

FIG. 5 is a conceptual diagram for illustrating embodiments of processes according to embodiments. These processes may start from at least two ECG signals, such as a set 510 of the previously described ECG signals 311, 312, 313, 314, 315, 316. These processes aim at using the most appropriate ECG signals for rhythm analysis and making a determination of whether to shock or not.

In embodiments of FIG. 5, one may optionally use one of discarding processes 525, in which one or more of the ECG signals of set 510 is discarded. In the example of FIG. 5, ECG signal 313 is shown as discarded; in other examples, other sets of the ECG signals may be discarded. Discarding according to one of processes 525 is described in more detail later in this document. If, after discarding, only one of the ECG signals remains, then a shock/no shock determination 535 can be made.

In embodiments of FIG. 5, one may optionally use one of combination processes 545 for the ECG signals of set 510. One of combination processes 545 may be used whether one of discarding processes 525 has been used first or not. In combination processes 545 two or more of the ECG signals of set 510, or their results, are combined to make an aggregate shock/no shock determination 555. Accordingly, combination processes 545 may be performed directly from the ECG signals 311, 312, 313, 314, 315, 316 of set 510. Or, combination processes 545 may be performed from the ECG signals remaining after processes 525, if there are two or more of them remaining. Combination according to one of processes 545 is described in more detail later in this document.

Figure 6:
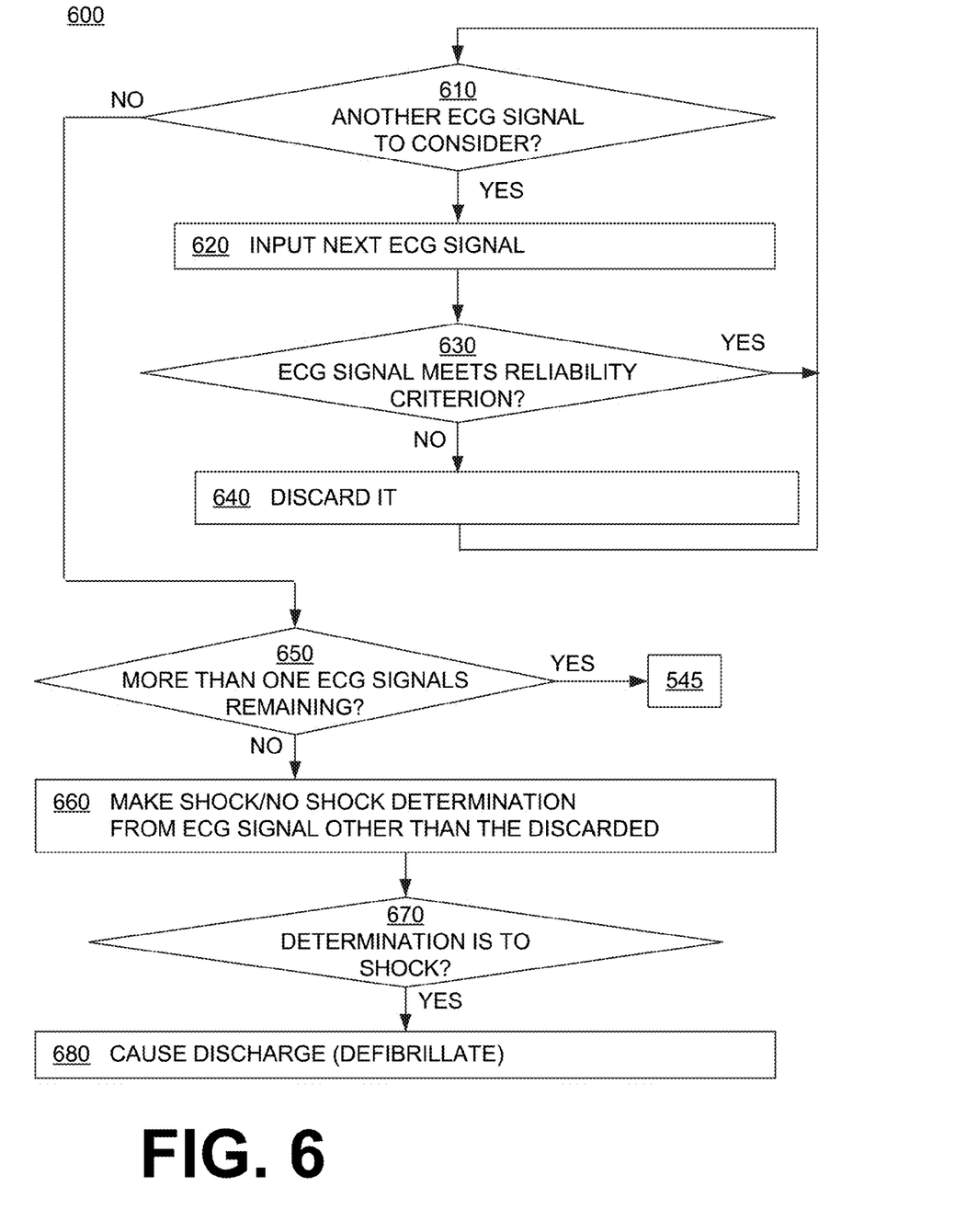
FIG. 6 is a flowchart for illustrating methods according to embodiments.

FIG. 6 shows a flowchart 600 for describing methods according to embodiments. The methods of flowchart 600 may also be practiced by embodiments described elsewhere in this document.

In flowchart 600, the group of operations 610, 620, 630, 640 can implement embodiments for discarding processes 525. According to an operation 610, it can be inquired whether there is another ECG signal to consider, for example from set 510. If yes, then according to another operation 620, then a next one of the ECG signals may be input. According to another operation 630, it can be decided whether the input ECG signal meets a reliability criterion, as will be described later in this document. If not, then according to another operation 640, the input ECG signal may be discarded, i.e. no longer considered.

Once all appropriate signals have been considered, execution may proceed from operation 610 to another operation 650, where it is inquired whether one or more than one ECG signals remain after the discarding. This number of remaining ECG signals may depend both on circumstances and also on the methodology of discarding according to a reliability criterion, as will be understood from the examples below.

In some embodiments, the reliability criterion is that the ECG signal has a reliability value that is higher than a threshold. The reliability value may be computed as a mathematical statistic to decide whether the reliability criterion is met or not. Accordingly, it will not be known in advance whether any, some, or all of the ECG signals in set 510 will be discarded, and therefore whether there will be any remaining signals for making the shock/no shock determination. If no ECG signals remain, then a shock/no shock determination might not be made, and the WCD system may instead prompt for better sensing conditions, e.g. ask that movement stops, etc.

Figure 7:
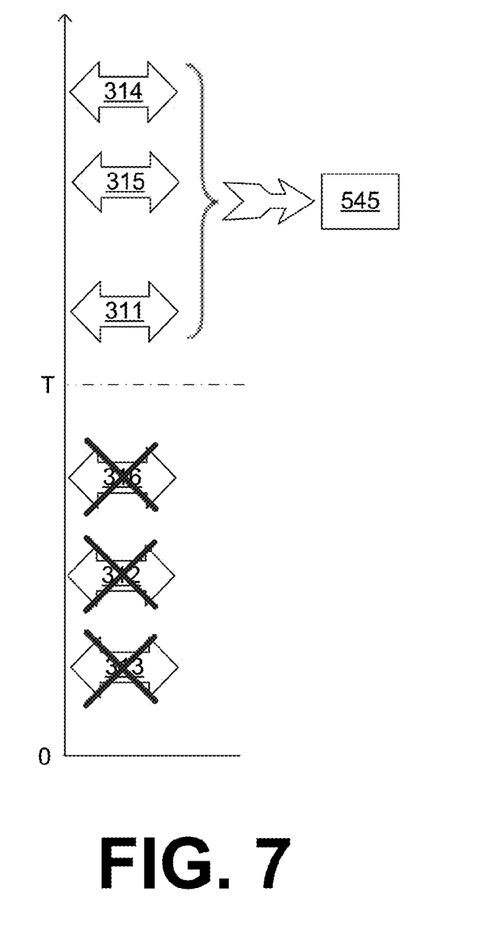
FIG. 7 is a conceptual diagram for illustrating an example of how a decision can be made to discard at least one ECG signal according to embodiments.

For instance, FIG. 7 shows an example where ECG signals 314, 315, 311 meet the reliability criterion, while ECG signals 316, 312, 313 do not and are thus shown as discarded. In the example of FIG. 7, meeting the reliability criterion is determined by the fact that ECG signals 314, 315, 311 have a reliability value that is higher than threshold T, while the rest do not. Accordingly, in this instance, the ECG determination can be made from the non-discarded ECG signals 314, 315, 311 according to one of processes 545.

In other embodiments, the reliability criterion can be that the ECG signal has a reliability value that is higher than the reliability value of another of the ECG signals. In other words, the criterion can be relative, among the ECG signals. In such embodiments, discarding may continue until all the ECG signals are discarded except a specified number, such as one, two, three, etc. For implementing these embodiments, flowchart 600 would have to be modified accordingly. For example, the reliability criterion can be that the ECG signal that is not discarded is the one that has a higher reliability value than the other ECG signals. The advantage is that only one ECG signal remains, and thus making a shock/no shock determination 535 can be done more simply, as is known.

Figure 8:
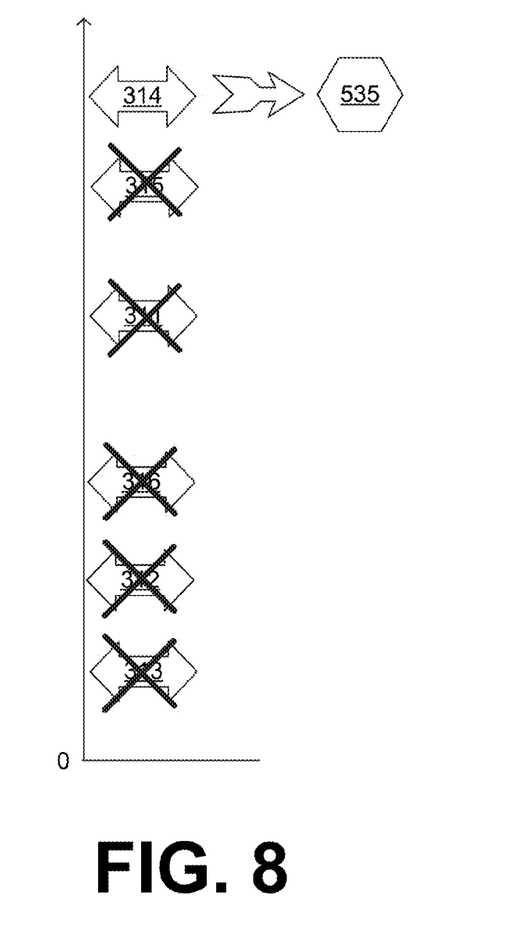
FIG. 8 is a conceptual diagram for illustrating an example of how a decision can be made to discard all except one ECG signal according to embodiments.

For instance, FIG. 8 shows an example of where ECG signal 314 remains, while all other ECG signals 315, 311, 316, 312, 313 are discarded. In the example of FIG. 8, ECG signal 314 is not discarded because it was the one that has the higher reliability value. A shock/no shock determination 535 can be made from single remaining ECG signal 314.

In these embodiments, discarding can proceed regardless of whether any threshold is met or not. Accordingly, the risk is that the single remaining ECG signal 314, while deemed the best available, will have a reliability value that is not higher than a threshold. Optionally, it can be further determined whether the remaining non-discarded ECG signal has a reliability value that is less than a threshold and, if so, not making a shock/no shock determination.

Returning to FIG. 6, therefore, at operation 650, if more than one non-discarded ECG signals remain, execution can proceed to processes 545. If only one non-discarded ECG signal remains, then, execution can proceed to another operation 660.

According to operation 660, a shock/no shock determination 535 can be made from one of the ECG signals that is not a discarded ECG signal. That ECG signal may be the only remaining ECG signal. The determination can be made as is known in the art.

According to another operation 670, it may be inquired if the determination of operation 660 is to shock. If so, then according to another operation 680, a discharge circuit can be caused to discharge a stored electrical charge through at least two electrodes so as to defibrillate a patient.

Selective discarding of ECG signals is now described in more detail. In some instances, the reliability criterion is related to a noise of the ECG signal.

In some embodiments, the component or the wearable cardiac defibrillation system includes an implement (not shown). The implement can be configured to detect an ECG common voltage signal. In such embodiments, the reliability criterion for a certain ECG signal can be derived from a mathematical correlation between the ECG common voltage signal and the certain ECG signal. This may help, because a common-mode signal may cause artifacts to appear on the ECG signals that are differential, i.e. between electrodes. A perfect differential amplifier in a circuit that detects an ECG signal would not have this problem, but real-life differential amplifiers have a limited common-mode rejection. The reliability criterion could be that the mathematical correlation is less than a threshold, and the reliability values would be inverted from what is suggested in FIGS. 7 and 8. If ECG signals were ranked, the one with the lowest correlation would be considered to have the lowest noise and would thus be chosen for rhythm monitoring.

In some embodiments, an impedance signal of the patient is captured along with the ECG signals. In such embodiments, the reliability criterion for a certain ECG signal can be derived from a mathematical correlation between the impedance signal and the certain ECG signal. Again, the reliability criterion could be that the mathematical correlation is less than a threshold.

Impedance could be monitored in a number of contexts. In some embodiments, impedance along multiple vectors is monitored, even all the vectors that would correspond to the ECG signals, if available. In some embodiments, the impedance signal could be derived from a single vector impedance measurement made between two electrodes, or it could be an impedance measurement found by a combination between different sets of electrodes. The combination could be a root of the sums of the squares (RSS). In some embodiments, the impedance of the electrode-skin interface of each electrode is also monitored.

In some embodiments, the component or the wearable cardiac defibrillation system includes an accelerometer, which could be within outside monitoring device 180 or internal monitoring device 281. The accelerometer can be configured to generate an acceleration signal. In such embodiments, the reliability criterion for a certain ECG signal can be derived from a mathematical correlation between the acceleration signal and the certain ECG signal. The accelerometer can be, for example, a three-axis accelerometer, each axis providing a channel. The correlation could be performed separately against each of the three channels, or it could be performed on a mathematical combination of the three channels, such as an RSS combination.

As described above, the mathematical correlation could be a cross-correlation. The cross-correlation could be a mathematically literal cross-correlation, or it may be a pseudo cross-correlation, an association of some sort. A literal cross-correlation would involve taking a point by point product of the two signals, and then taking the sum.

A pseudo cross-correlation could be any function that associates activity on one channel with activity on another channel. In some embodiments, signals could be simplified before the point-by-point multiplication of the cross-correlation is performed. For example, the absolute value of the signals could be taken. For another example, each signal could be low-pass filtered. A pseudo cross-correlation may also look for similarities in the frequency domain. This might be done by taking a Fast Fourier Transform (FFT) of each signal and examining the amount of overlap. Or, it is possible that alignment between the peak frequency of each signal might be sufficient to indicate noise on a particular channel. Yet another possibility is to look at the coherence between the two signals.

In embodiments, the decision of whether to discard an ECG signal or not is made based on whether a cardiac feature is recognized in one of the ECG signals, which would make that ECG signal a more reliable indicator. For example, either one of waveforms 411, 412 corresponds to a signal of high reliability.

In embodiments, the decision of whether to discard an ECG signal or not is made from a measured amplitude of the ECG signal. This can be performed in a number of ways.

For one example, the reliability criterion can be met depending on how well the measured amplitude matches a reference amplitude. The reference amplitude can be known in advance—for example it may be the amplitude of a QRS complex that is typical for a patient, or has been measured in advance for specific patient 82, perhaps at the time that the WCD system was fitted to them.

For another example, the reliability criterion can be met depending on how large is a ratio of a peak value to a median value of the ECG signal. This works because it takes advantage of the characteristics of a QRS complex, such as is shown in waveform 411. QRS complexes have a high such ratio; sinusoidal noise tends to have a lower ratio. It has the advantage that it would bias the channel selection toward the channel with the highest apparent QRS complexes.

In some embodiments, at least a certain one of the ECG signals is analyzed for a detected patient heart rate. Of course, a patient heart rate will not always be detected but if it is, such as in waveform 412, it is a rather good indication. Then the individual shock/no shock recommendation from the certain ECG signal can be to shock, if the detected patient heart rate is above a threshold, and not to shock otherwise. That threshold could be, for example, 200 bpm.

In some embodiments, the ECG signals can be compared to each other, for example by taking a mathematical correlation between two of them in pairs. If two of them show cardiac features concurrently, that can be evidence that they are both reliable, only one of them need be used, and the rest can be discarded. Of course, similarity can be while allowing for different amplitude scale, different other aspects for different placement of electrodes, etc. Plus, sometimes noise artifacts can be temporally similar along different vectors especially if they share the same electrode, and should not be allowed to confuse the analysis. In these embodiments, therefore, the reliability criterion for an ECG signal might not be met, if two others of the ECG signals have an aspect similar to each other, because these two other signals may be preferred.

Combination processes 545 of FIG. 5 are now described in more detail. An embodiment of these processes can be used for making an aggregate shock/no shock determination 555 from two or more ECG signals.

Figure 9:
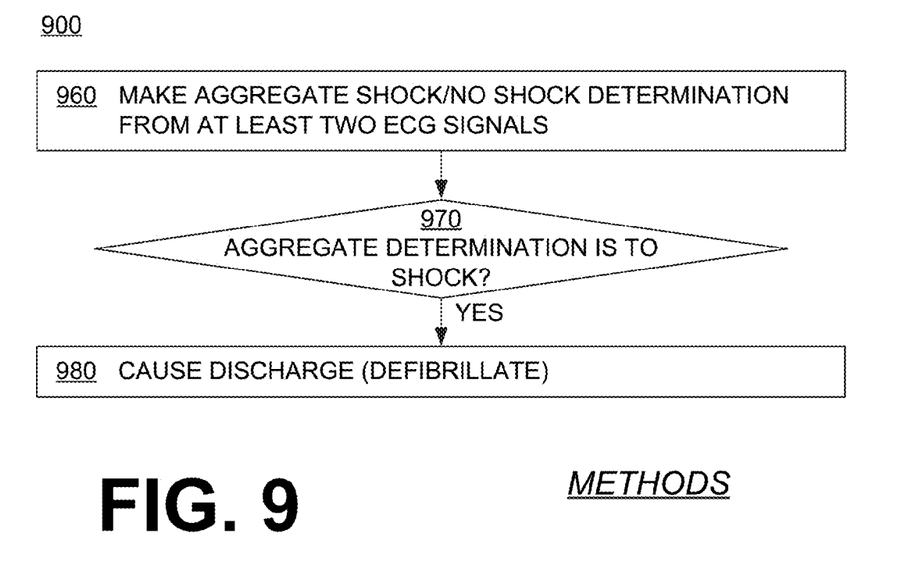
FIG. 9 is a flowchart for illustrating methods according to embodiments.

FIG. 9 shows a flowchart 900 for describing methods according to embodiments. The methods of flowchart 900 may also be practiced by embodiments described elsewhere in this document. Flowchart 900 can implement embodiments for combination processes 545.

According to an operation 960, an aggregate shock/no shock determination 555 can be made from at least two of the ECG signals, as described later. According to another operation 970, it may be inquired whether the aggregate determination of operation 960 is to shock. If so, then according to another operation 980, a discharge circuit can be caused to discharge a stored electrical charge through at least two electrodes so as to defibrillate a patient.

Making the aggregate shock/no shock determination is now described in more detail. There are a number of ways this may be performed. In many embodiments, an individual shock/no shock recommendation is made from the respective ECG signals, for example is if each of them were the only ECG signal. Then the aggregate shock/no shock determination can be made from the individual recommendations, by combining them. There are many such ways to combine, and examples are described.

In some embodiments, the aggregate shock/no shock determination is to shock if any of the individual recommendations is to shock. This can be implemented if it is desirable to bias the WCD system in favor of shocking, e.g. to ensure a very high sensitivity. These embodiments can be complemented with those described above, e.g. where the heart rate is detected to be above a threshold.

In some embodiments, the aggregate shock/no shock determination is to not shock if any of the individual recommendations is to not shock. This can be implemented if it is desirable to bias the WCD system against shocking, e.g. to avoid disturbing the patient with shocks, some of which might not be needed. These embodiments can be complemented with those described above, e.g. where the heart rate is detected to be below a threshold, and/or where ECG signals can be discarded based on amplitude. For example, at least one of the ECG signals can be discarded if its measured amplitude does not meet a reliability criterion, which would bias leaving in ECG signals with a possible QRS complex as described above, especially where the reliability criterion is met depending on how large is a ratio of a peak value to a median value of the ECG signal. In these cases, the ECG signals used to make the aggregate shock/no shock determination do not include the discarded ECG signal.

In some embodiments, the aggregate shock/no shock determination is made from a statistic of the individual shock/no shock recommendations. The statistic could be a simple majority voting. In such cases, all ECG signals might be discarded except an odd number, such as the top three most reliable ones.

In some embodiments, individual shock/no shock recommendations are made in the form of respective certainty values from the ECG signals. For example, these certainty values, instead of a simple shock/no-shock result. Such algorithms might, for example, produce a result in which a positive number is shockable, a negative number is non-shockable, and zero is indeterminate. In these embodiments, the aggregate shock/no shock determination can be made from a numeric combination of the certainty values. An example is now described.

Figure 10:
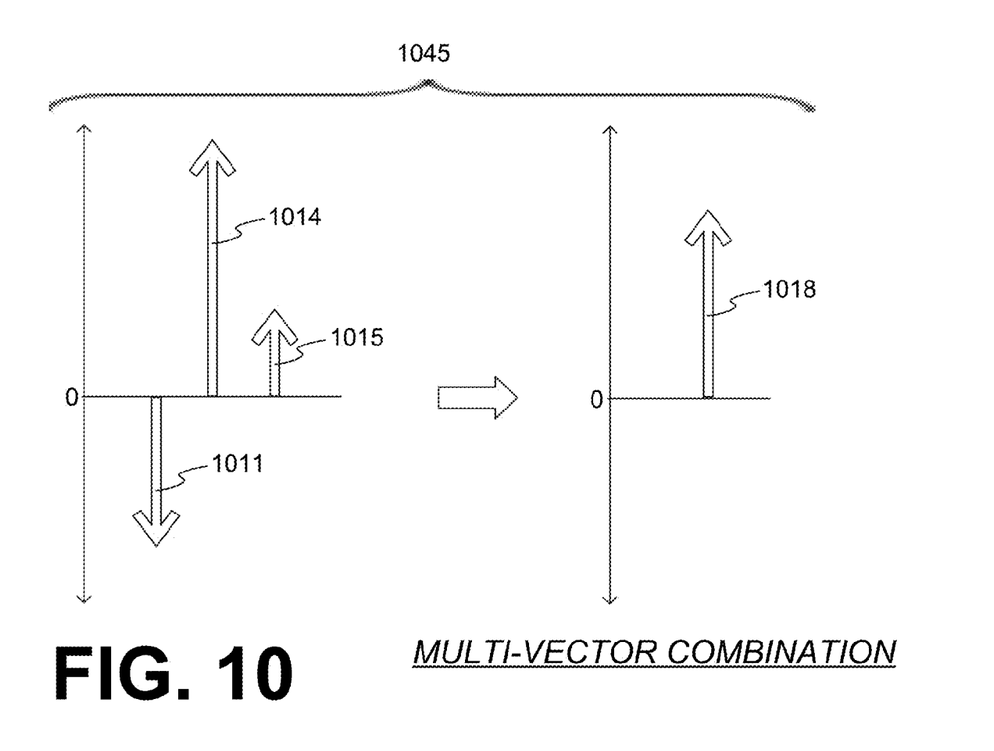
FIG. 10 is a conceptual diagram for illustrating how a sample combination can be made from individual decisions according to embodiments.

FIG. 10 is a conceptual diagram for illustrating how a sample combination can be made from individual decisions according to embodiments. Three ECG signals have been analyzed, and have resulted in making three individual shock/no shock recommendations in the form of numerical certainty values that are plotted as vectors 1011, 1014, 1015. Within a combination process 1045, the three vectors are added into a resultant vector 1018. Since it is positive, the aggregate determination will be to shock.

There are other ways for combining the certainty values. For example, the median value may be consulted. In the example of FIG. 10, the median value would be vector 1015, resulting in an aggregate shock determination. In addition, at least one of them can be multiplied by a confidence coefficient before the aggregate shock/no shock determination is made. The confidence coefficient can be implemented in a number of ways.

In some embodiments, the confidence coefficient is learned from parameters of the signal itself, such as the amplitude as described above. In particular, at least one of the ECG signals can be discarded if its measured amplitude does not meet a reliability criterion, and the ECG signals used to make the aggregate shock/no shock determination do not include the discarded ECG signal.

In some embodiments, the confidence coefficient is learned from a history of the ECG signal. This could be done by running multiple successive analyses on each channel that generates an ECG signal. If one channel produces a consistent result over time, either shock or no-shock, then it might be considered more reliable than a channel that produces an inconsistent result over time. If a numerical value is calculated for the shock decision, then the channel with the least numerical spread might be considered the most reliable. The numerical spread might be estimated, for example, by examining the range of values, by examining the variance of the data, or by examining the standard deviation.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases. This element or feature can be implemented in any number of ways, as will be apparent to a person skilled in the art after reviewing the present disclosure, beyond any examples shown in this example.

The following claims define certain combinations and subcombinations of elements, features and steps or operations, which are regarded as novel and non-obvious. Additional claims for other such combinations and subcombinations may be presented in this or a related document. When used in the claims, the phrases "constructed to" and/or "configured to" reach well beyond merely describing an intended use, since such claims actively recite an actual state of construction and/or configuration based upon described and claimed structure.

What is claimed is:

1. A component of a wearable cardiac defibrillation (WCD) system, the WCD system including a support structure configured to be worn by a patient, sensing electrodes configured to capture at least two ElectroCardioGram (ECG) signals of the patient, and defibrillation electrodes configured to transport electrical charge, the component comprising:
  an energy storage module configured to store an electrical charge;
  a discharge circuit coupled to the energy storage module; and
  a processor configured to:
    make a certain aggregate shock/no shock determination from at least two of the ECG signals, in which respective individual shock/no shock recommendations are made from each of the at least two of the ECG signals, the respective individual shock/no shock recommendations having a form of respective certainty values, and the certain aggregate shock/no shock determination is made from a statistic of the respective certainty values, and
    cause, if the certain aggregate shock/no shock determination is to shock, the discharge circuit to discharge the stored electrical charge through the defibrillation electrodes so as to defibrillate the patient.

2. The component of claim 1, in which
at least one of the ECG signals is discarded if it does not meet a reliability criterion, and
the at least two of the ECG signals from which the certain aggregate shock/no shock determination is made do not include the discarded ECG signal.

3. The component of claim 1, in which
the certain aggregate shock/no shock determination is to shock if any of the respective individual recommendations is to shock.

4. The component of claim 3, in which
at least a certain one of the at least two ECG signals is analyzed for a detected patient heart rate, and
the respective individual shock/no shock recommendation from the certain ECG signal is to shock if the detected patient heart rate is above a threshold.

5. The component of claim 1, in which
the certain aggregate shock/no shock determination is to not shock if any of the respective individual recommendations is to not shock.

6. A component of a wearable cardiac defibrillation (WCD) system, the WCD system including a support structure configured to be worn by a patient, sensing electrodes configured to capture at least two ElectroCardioGram (ECG) signals of the patient, and defibrillation electrodes configured to transport electrical charge, the component comprising:
  an energy storage module configured to store an electrical charge;
  a discharge circuit coupled to the energy storage module; and
  a processor configured to:
    make a certain aggregate shock/no shock determination from at least two of the ECG signals, in which
      respective individual shock/no shock recommendations are made from each of the at least two of the ECG signals, and
      at least a certain one of the at least two ECG signals is analyzed for a detected patient heart rate and the respective individual shock/no shock recommendation from the certain ECG signal is to shock if the detected patient heart rate is above a threshold, and
    cause, if the certain aggregate shock/no shock determination is to shock, the discharge circuit to discharge the stored electrical charge through the defibrillation electrodes so as to defibrillate the patient.

7. The component of claim 6, in which
at least one of the ECG signals is discarded if it does not meet a reliability criterion, and
the at least two of the ECG signals from which the certain aggregate shock/no shock determination is made do not include the discarded ECG signal.

8. The component of claim 6, in which
an amplitude of a certain one of the ECG signals is measured, and
the at least two of the ECG signals from which the certain aggregate shock/no shock determination is made do not include the certain ECG signal, if the measured amplitude of the certain ECG signal does not meet a reliability criterion.

9. The component of claim 6, in which
the certain aggregate shock/no shock determination is made from the respective individual recommendations.

10. The component of claim 6, in which
the certain aggregate shock/no shock determination is to not shock if any of the respective individual recommendations is to not shock.

11. The component of claim 6, in which
the certain aggregate shock/no shock determination is made from a statistic of the respective individual shock/no shock recommendations.

12. The component of claim 6, in which
the certain aggregate shock/no shock determination is to shock if any of the respective individual recommendations is to shock.

* * * * *

UNITED STATES PATENT AND TRADEMARK OFFICE
CERTIFICATE OF CORRECTION

PATENT NO. : 9,757,581 B2
APPLICATION NO. : 15/142656
DATED : September 12, 2017
INVENTOR(S) : Joseph L. Sullivan, Robert P. Marx, Jr. and David P. Finch

Page 1 of 1

It is certified that error appears in the above-identified patent and that said Letters Patent is hereby corrected as shown below:

On the Title Page

On page 2 item (60) Related U.S. Application Data delete "Provisional application No. 61/002,841, filed on May 13, 2014" and replace with -- Provisional application No. 61/992,841, filed on May 13, 2014 --.

Signed and Sealed this
Eighth Day of April, 2025

Coke Morgan Stewart
*Acting Director of the United States Patent and Trademark Office*